US007810643B2

(12) United States Patent
Firestone et al.

(10) Patent No.: US 7,810,643 B2
(45) Date of Patent: *Oct. 12, 2010

(54) MEMANTINE TITRATION/COMPLIANCE DOSAGE METHODS

(75) Inventors: Bruce A. Firestone, Irvine, CA (US); John Jacob Vander Zanden, Edina, MN (US); Rodney J. Terwilliger, Buena Park, CA (US); Janet K. Cheetham, Laguna Niguel, CA (US); Richard Kurjan, Huntington Beach, CA (US); Teresa Kuan, Placentia, CA (US); Chin-Ming Chang, Tustin, CA (US); J. Abraham M. Le Espiritu, Oceanside, CA (US)

(73) Assignee: Allergan, Inc., IRvine, CA (US)

( * ) Notice: Subject to any disclaimer, the term of this patent is extended or adjusted under 35 U.S.C. 154(b) by 815 days.

This patent is subject to a terminal disclaimer.

(21) Appl. No.: 11/483,039

(22) Filed: Jul. 7, 2006

(65) Prior Publication Data

US 2006/0278557 A1 Dec. 14, 2006

Related U.S. Application Data

(63) Continuation-in-part of application No. 10/622,170, filed on Jul. 16, 2003, now Pat. No. 7,086,532.

(51) Int. Cl.
*B65D 83/04* (2006.01)
*A61K 9/00* (2006.01)
*A61K 31/13* (2006.01)

(52) U.S. Cl. .................. 206/534; 206/531; 206/532; 206/539; 424/400; 514/662

(58) Field of Classification Search .............. 206/528, 206/531–532, 534–534.2, 538–539; 424/400; 514/662
See application file for complete search history.

(56) References Cited

U.S. PATENT DOCUMENTS

| 2,415,859 | A | 2/1947 | Ancker |
| 3,099,352 | A | 7/1963 | Aven |
| 3,225,913 | A | 12/1965 | Lee |
| 3,568,828 | A | 3/1971 | Lerner |
| 3,738,480 | A | 6/1973 | Chesley |
| 3,826,222 | A | 7/1974 | Romick |
| 3,921,806 | A | 11/1975 | Wawracz |

(Continued)

FOREIGN PATENT DOCUMENTS

CA 2218470 12/1999

(Continued)

*Primary Examiner*—Bryon P Gehman
(74) *Attorney, Agent, or Firm*—Kevin J. Forrestal; John E. Wurst; Doina G. Ene

(57) ABSTRACT

A titration package and method for enabling compliance with a regimen of changing dosage of medication over a period of time includes a backing having an array of receivers with the array including a plurality of columns and a plurality of rows. A plurality of sets of Memantine tablets are provided with each tablet set having a common dose of medication and a different does than a tablet of a different set. Each set of tablets is disposed in receivers of one having an adjacent row and an adjacent column. Indicia is provided and disposed adjacent to the columns and rows for displaying common days and successive weeks.

6 Claims, 3 Drawing Sheets

U.S. PATENT DOCUMENTS

| | | |
|---|---|---|
| RE29,705 E | 7/1978 | Compere |
| 4,148,273 A | 4/1979 | Hollingsworth et al. |
| 4,473,156 A | 9/1984 | Martin |
| 4,473,884 A | 9/1984 | Behl |
| 4,617,557 A | 10/1986 | Gordon |
| 4,706,815 A | 11/1987 | Curtis et al. |
| 4,883,180 A | 11/1989 | Humphrey et al. |
| 4,958,736 A | 9/1990 | Urheim |
| D330,331 S | 10/1992 | Hsiao |
| 5,288,107 A | 2/1994 | Johnson et al. |
| D383,668 S | 9/1997 | Siegel et al. |
| 5,747,545 A | 5/1998 | Lipton |
| 5,752,235 A | 5/1998 | Kehr et al. |
| 5,922,773 A | 7/1999 | Lipton et al. |
| 6,047,829 A | 4/2000 | Johnstone et al. |
| 6,169,707 B1 | 1/2001 | Newland |
| 6,375,956 B1 | 4/2002 | Hermelin et al. |
| 6,411,567 B1 | 6/2002 | Niemiec et al. |
| 6,471,645 B1 | 10/2002 | Warkentin et al. |
| 6,491,211 B1 | 12/2002 | Evans et al. |
| 6,564,945 B1 | 5/2003 | Weinstein et al. |
| 6,651,816 B2 | 11/2003 | Weinstein |
| 2004/0176381 A1 | 9/2004 | Walsh |
| 2004/0254251 A1 | 12/2004 | Firestone et al. |

FOREIGN PATENT DOCUMENTS

| | | |
|---|---|---|
| EP | 0 852 208 A1 | 7/1998 |
| WO | WO 97/03896 | 2/1997 |
| WO | WO 03/032891 A1 | 4/2003 |

FIG. 3.

Manufacturing Process Flow Diagram for Memantine HCl Tablets

MEMANTINE TITRATION/COMPLIANCE DOSAGE METHODS

CROSS REFERENCE TO RELATED APPLICATIONS

The present application is a continuation-in-part of U.S. Ser. No. 10/622,170 filed Jul. 16, 2003, now U.S. Pat. No. 7,086,532, issued on Aug. 8, 2006.

The present invention is generally directed to pharmaceutical dosage form including a titration package for enabling compliance with a regimen of changing dosage of medication over a period of time and is more particularly directed to a dosage pack for dosing of oral Memantine for the indication of preventing further nerve cell loss in glaucoma patients.

Glaucoma is characterized by damaged to the optic nerve which is typically accompanied by a decrease in normal vision field. An early sign of possible glaucomatous visual field loss is elevated interocular pressure.

In that regard, glaucoma has typically been treated by medically and/or surgically lowering elevated interocular pressure. Memantine and other compounds suitable for chronic administration should be administered to avoid adverse events associated with the drug, for example, patients prescribed Memantine therapy need to be titrated upwards from 5 mg of Memantine per day to a maintenance dose of either 10 mg or 20 mg per day. Memantine approved for other indications, such as Alzheimer's Dementia, also may require similar titration schedules to avoid drug-related adverse events.

The present invention is directed to a titration package for enabling compliance with a regimen of changing dosage of medication over a period of time and further provides for a method of treating a human patient to reduce damage to retinal ganglion cells associated with glaucoma utilizing the titration package in accordance with the present invention.

To avoid adverse effects associated with the drug, memantine is initially administered to the patient at a dose of 5 mg per day, which is gradually increased to a maintenance dose of either 10 mg or 20 mg per day. The dosage is increased by 5 mg biweekly until the maintenance dose is reached.

Currently two memantine products are marketed in Europe for the treatment of Alzheimer's Dementia. Both products, Axura® (Merz) and Ebixa® (Lundbeck) are marketed in packages of 10 mg tablets. The currently available products require the patient to track the dose that they are required to take according to how long they have been taking the drug, and to take ½ tablet, 1 tablet, 1½ tablets, or 2 tablets accordingly. Because the typical patient requiring this medication is using it to slow the progression of blindness or dementia, patients taking memantine are particularly susceptible to incorrect dosing with this type of graduated dose schedule. In particular, it is likely that the 5 mg and 15 mg doses will be especially problematic for patients because they are required to both choose the correct tablets and divide the 10 mg tablet in half. Furthermore, the patients must keep track of the half tablet left over after dividing the tablet for use in the next day. Finally, dividing a tablet introduces the possibility that the dose will not be consistent.

SUMMARY OF THE INVENTION

A titration package for enabling compliance with a regimen of changing dosage of medication over a period of time in accordance with the present invention generally includes a backing having an array of receivers with the array including a plurality of columns and a plurality of rows.

A plurality of sets of tablets are provided in the receivers. Each tablet in a set has a common dose of medication and a different dose than a tablet of a different set. Each set of tablets is disposed in receivers of one of an adjacent row and an adjacent column.

Indicia is provided and disposed adjacent the columns and rows for displaying common days and successive weeks. Thus, the package provides for a titration schedule which prevents adverse events as a result of mis-dosing. As a result, the package in accordance with the present invention provides for a safer and accordingly more beneficial method for enabling compliance with the regimen.

More particularly, in one embodiment of the present invention different sets of tablets are disposed in different rows with each row being indicated by a successive week and each column being indicated as a different day of the week. In this embodiment, the sets of tablets having increased doses are disposed in receivers in rows indicated as successive weeks. More specifically, the sets of tablets have 5 mg, 10 mg, 15 mg and 20 mg doses of Memantine.

In an alternative embodiment, different sets of tablets are disposed in different columns, with each column being indicated as a successive week and each row being indicated as a different day of the week.

In yet another embodiment of the present invention, the titration package for enabling compliance with a regimen of changing doses of medication over a period of time includes a backing having an array or receivers with the array including a plurality of columns and a plurality of rows. In this embodiment, a plurality of sets of tablets are provided with each set being disposed in receivers of a plurality of adjacent rows or a plurality of adjacent columns. This plurality may be two and each tablet in a set has a common dose of medication and a different dose than a tablet in a different set.

Preferably, in this embodiment pairs of adjacent rows have differing sets of tablets. This enables the change of dosage over an eight-week period of time from 5 mg to 20 mg doses of Memantine.

It has been found that dosage forms of memantine that contain doses of memantine that are not 10 mg or 20 mg are useful in helping to overcome the difficulties described above. These dosage forms contain between 1 mg and 100 mg of memantine. Unlike other dosage forms of memantine containing a dose that is not 10 mg or 20 mg, these dosage forms are not prepared by the patient or the person administering the medication to the patient who divides a larger dose. In other words, the patient or the person administering the medication does not have to divide the dosage form to obtain the appropriate dose. While not intending to be limiting in any way, the present invention for example, provides for 5 mg and 15 mg tablets of memantine that are available to the patient or the person administering the drug to the patient in those forms, meaning that the patient does not have to divide a 10 mg tablet to obtain a 5 mg dose or take 1½ 10 mg tablets to obtain a 15 mg dose. Another significant contribution this invention makes to the art is that it allows a maintenance dose to be administered that is not 10 or 20 mg. For example, if a person needs more than 10 mg daily of memantine, but a 20 mg daily dose is undesirable, the person could receive a 15 mg maintenance dose without having difficulties with misdosing.

Accordingly, the present invention provides for a method for enabling compliance with a regimen of changing dosage of medication with the method comprising the steps of providing a backing having an array of receivers, with the array including a plurality of columns and a plurality of rows. The method further includes disposing a plurality of sets of tablets and the receivers with each tablet in the set having a common dose of medication and a different dose than a tablet of a different set. Each set is disposed in receivers of one of an adjacent row and an adjacent column. The method finally includes a step of providing indicia adjacent the columns and rows indicating common days and successive weeks.

A concomitant method in accordance with the present invention provides for a method of treating a human patient to reduce damage to retinal ganglion cells associated with glaucoma with the method comprising providing a titration package for enabling compliance with a regimen of changing dosage of medication over a period of time. The package includes the elements hereinabove recited and further the medication comprises Memantine.

BRIEF DESCRIPTION OF THE DRAWINGS

The present invention may be more clearly understood with reference to the following detailed description in conjunction with the appended drawings of which:

FIG. 3 is a representation similar to the titration package shown in FIG. 2 showing an alternative arrangement of days and successive weeks, as will be hereinafter described;

DETAILED DESCRIPTION

The titration package and method in accordance to the present invention is particularly useful for the dosage of oral medication for infirmed and elderly patients and accordingly the manipulation of tablets enabled by the present invention and tracking of compliance with a titration schedule is a great advantage. In the case of treatment of glaucoma, and the use of a medicament, such as, for example Memantine, the progression of blindness also demands a need for the present invention.

Figure 1:
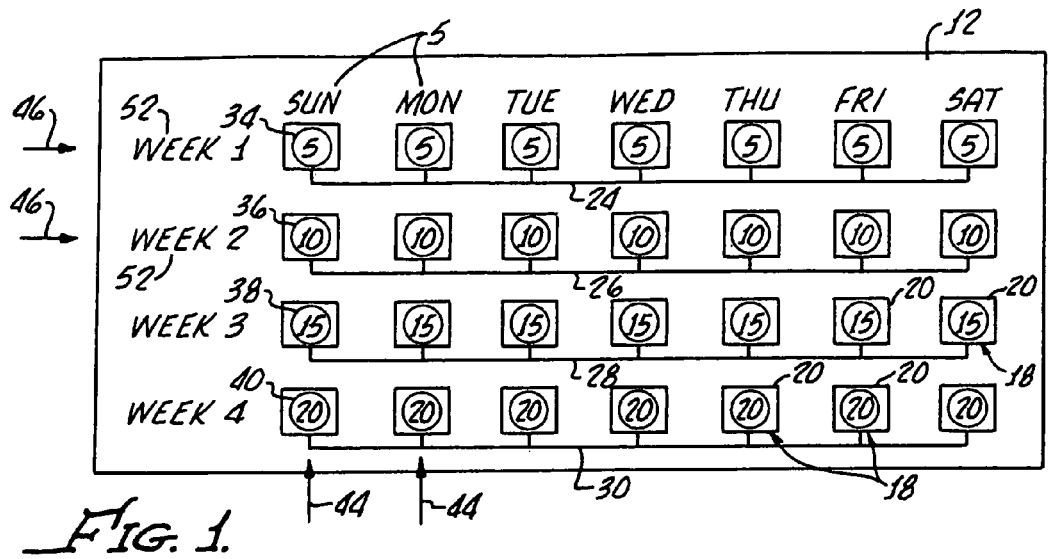
FIG. 1 is a representation of a titration package in accordance with the present invention for enabling compliance with a regimen of changing dosage of medication over a four-week period of time.

With reference to FIG. 1, there is represented a titration package 10 for enabling compliance with a regimen of changing dosage of medication over a period of time, for example four weeks with the package 10 including a backing 12 which includes an array 18 of receivers holding a plurality of sets 24, 26, 28, 30 of tablets 34, 36, 38, 40.

The receivers 20 may be conventional, rupturable blisters as, for example, as set forth in U.S. RE29,705 which is to be incorporated herewith in its entirety for the purpose of describing the type of rupturable receivers suitable for use with the present invention.

The backing 12 may be any suitable plastic or paperboard backing and may be incorporated into protective coverings, not shown, such as, for example, shown in U.S. Pat. No. 6,047,829. This patent is to also be incorporated herewith in its entirety by this specific reference thereto for showing a backing and dispensing package construction suitable for use in the present invention.

With continued reference to FIG. 1, the array 18 of receivers 20 includes a plurality of columns indicated by the arrows 44 and a plurality of rows indicated by the arrows 46. Indicia 50, 52 is provided and disposed adjacent the columns 44 and rows 46, preferably on the backing 12 displays common days and successive weeks.

As shown in FIG. 1, different sets are disposed in different rows 46 as indicated by week 1, week 2, week 3, and week 4. The number following the indicia "week" indicating successive weeks and the columns 44 indicated as Sunday, Monday, Tuesday, Wednesday, Thursday, Friday, and Saturday indicating different days of the week.

With regard to the treatment of glaucoma, the set 24 includes 5 mg of Memantine, the set 26 includes tablets of 10 mg of Memantine, the set 28 includes tablets of 15 mg of Memantine, and the set 30 includes tablets of 30 mg of Memantine arranged in the rows 46 indicated as week 1, week 2, week 3, and week 4. In accordance with the present invention, a patient utilizing the package and method of the present invention is titrated from a 5 mg dose to a 20 mg dose of the Memantine.

In use, a patient beginning the regimen may start on any given day of the week, for example, Tuesday and progressively take the tablets by rupturing the receivers 20 along a row until all of the tablets 34 have been dispensed. At that time, the patient begins week 2 of the regimen by taking the tablets 36 disposed in the row 46 indicated by the indicia, week 2.

Thus, the arrangement and dosages of the tablets therein enables compliance with the regimen of changing the dosage of the medication over the period of time, four weeks as indicated in FIG. 1.

Figure 2:
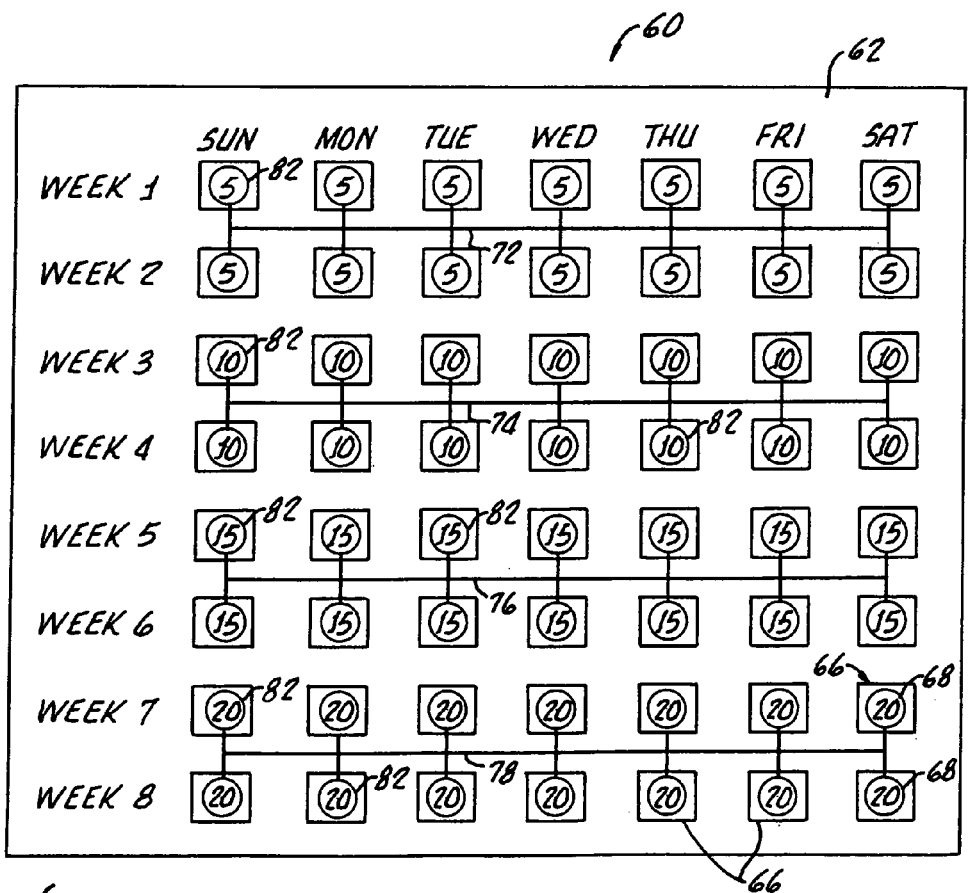
FIG. 2 is a representation of a titration package similar to that shown in FIG. 1 enabling compliance with a regimen of changing dosage of medication over a period of eight weeks.
Figure 4:
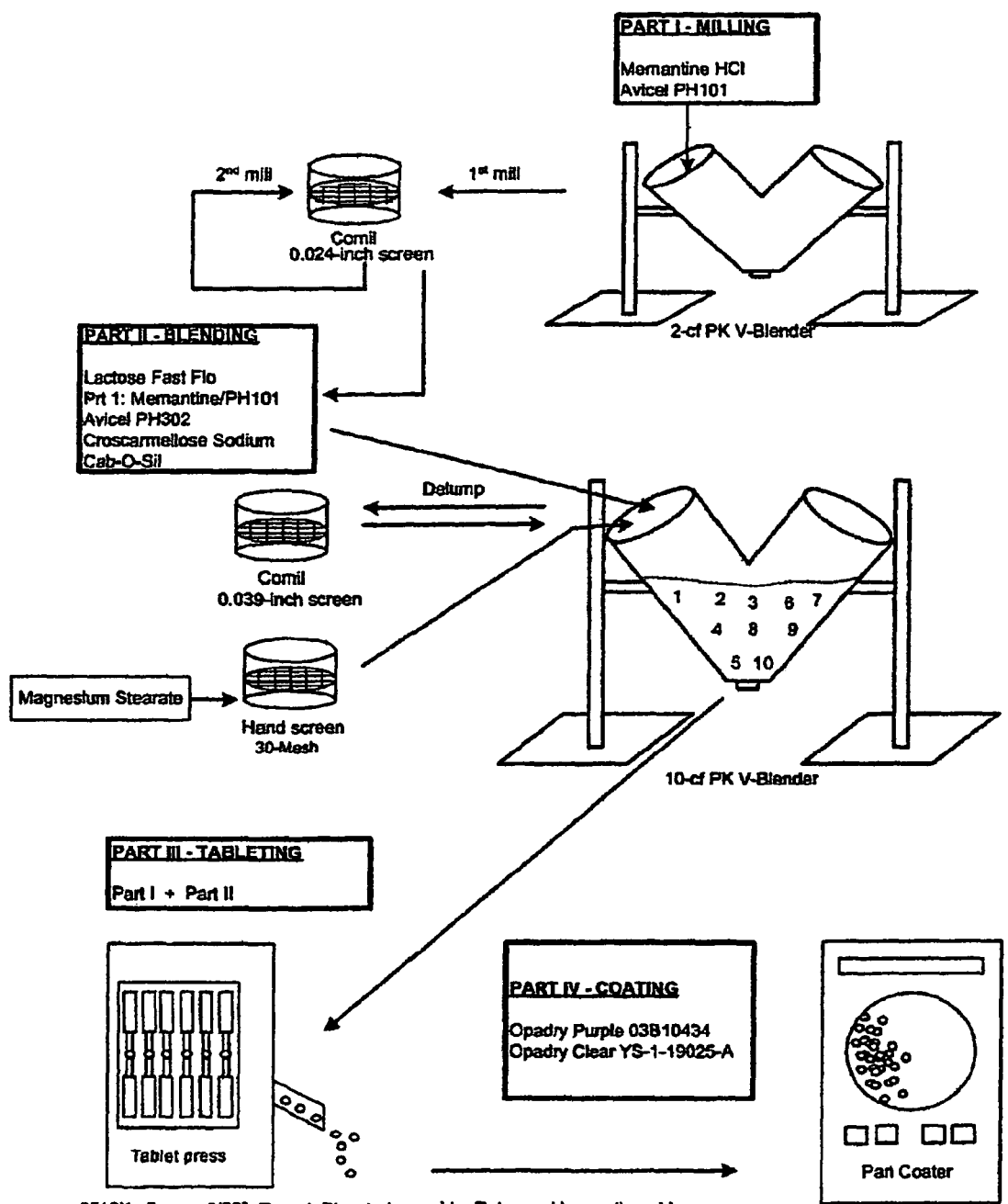
FIG. 4 shows the manufacturing process diagram for the 175 Kg process for Memantine HCl tablets.

With reference to FIG. 2, there is shown an alternative embodiment, or package, 60 in accordance with the present invention for enabling compliance with a regimen of changing dosage of medication over a period of 8 weeks. In this embodiment, a backing 62 is provided with an array 66 of receivers 68 with the array being arranged in rows indicated by the indicia, "week 1-8" and columns indicated as "Sun-Sat".

Figure 3:
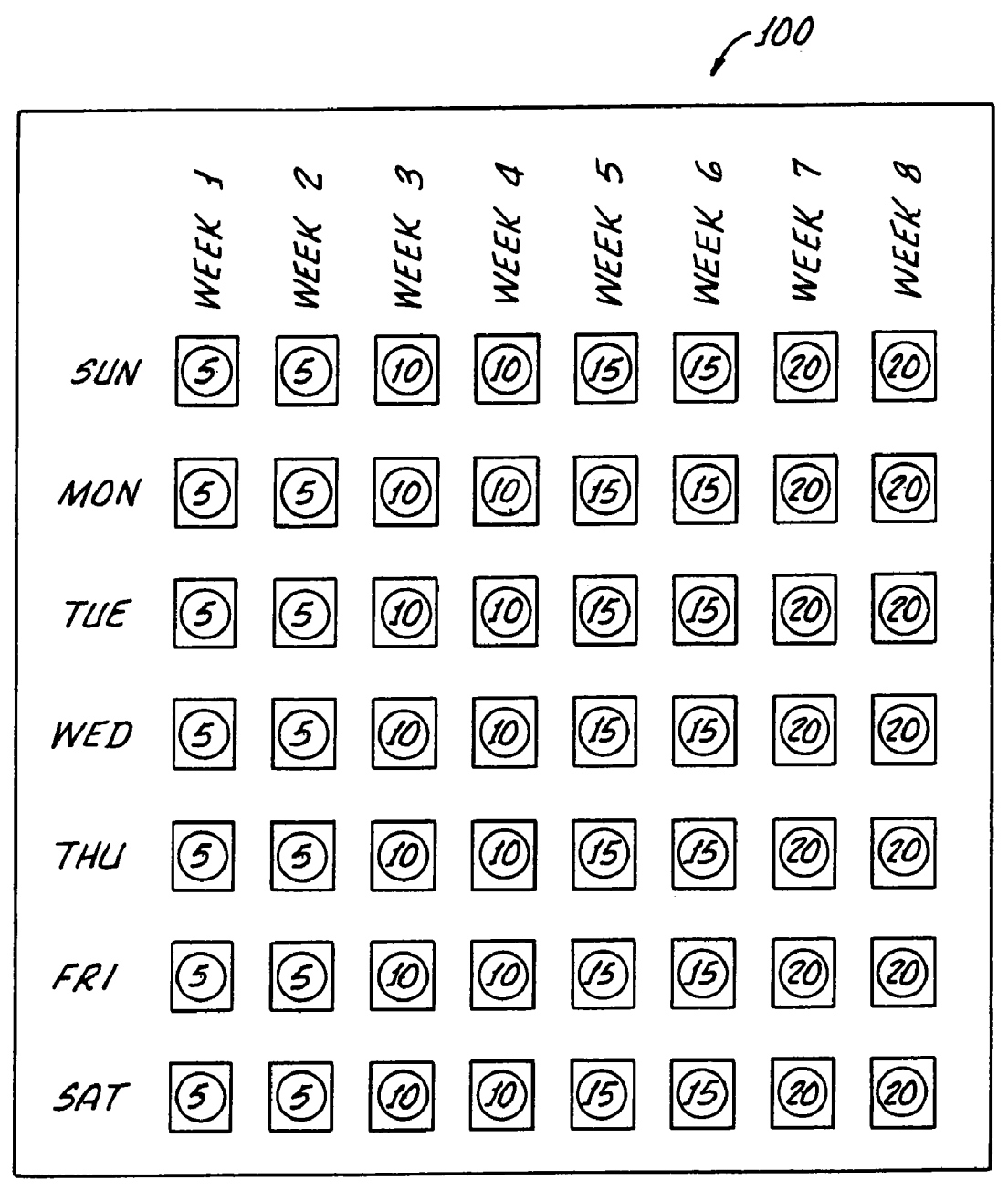

In this embodiment, different sets 72, 74, 76, 78 of tablets 82 are disposed in adjacent rows as shown in FIG. 2 or an adjacent columns as shown in the embodiment 100 of FIG. 3. Character references have been omitted from FIG. 3 to reduce redundancy in description. It should be clear that the embodiment of 60 and 100 are identical except for the arrangement of columns and rows.

In a method of treating a human patient in accordance with the present invention to reduce damage to retinal ganglion cells associated with glaucoma, the titration packages 60, 100 enable compliance with a regimen of changing dosage of medication over a period of time as hereinabove described in connection with the package 10 shown in FIG. 1.

The patient beginning on any of the week completes the removal and use of tablets in a corresponding week in adjacent rows or column before proceeding to the next pair of adjacent rows or columns in a manner as described hereinabove in connection with the embodiment 10 shown in FIG. 1.

Another aspect of the present invention relates to an oral dosage form containing between 1 mg and 100 mg of memantine, wherein at least some of the dosage forms do not contain 10 mg of memantine, and wherein said dosage form is not prepared by the patient or a person administering the drug to the patient who divides the dosage form containing a larger dose of memantine. Preferably, said oral dosage form contains 5 mg, 15 mg or 20 mg of memantine, where the particular dose of memantine used in relation to this invention is determined by the required dose of the patient according to the dosage schedule and titration package described above.

In another aspect of this invention the oral dosage form is a solid dosage form, preferably a tablet.

Still another embodiment of this invention relates to a method of administering memantine to a patient in amount that is not 10 mg, comprising administering to the patient an oral dosage form of memantine, wherein said dosage form is not prepared by the patient or a person administering the drug to the patient who divides the dosage form containing a larger dose of memantine.

Another aspect of this invention relates to a packaged pharmaceutical product comprising individual oral dosage forms of memantine which contain 5 mg, 15 mg, or 20 mg of memantine.

Preferably the packaged pharmaceutical product comprises individual oral dosage forms containing 5 mg of memantine, 10 mg of memantine, 15 mg of memantine, and 20 mg of memantine.

In another preferred embodiment of this invention the packaged pharmaceutical product comprises individual oral dosage forms containing 5 mg of memantine and 10 mg of memantine.

In certain cases, the initial administration of 5 mg of memantine, or the increase in the dosage by 5 mg increments, may be more than can be tolerated by the patient. Another aspect of this invention relates to a method of treating a patient with memantine, comprising a. administering a gradually increasing dose of memantine to said patient until the maintenance dose is reached, and
b. continuing to administer said maintenance dose on a regular basis as long as memantine is needed, wherein the maintenance dose is reached in a sufficiently long period of time to significantly reduce adverse events, wherein the increment in which the dose of memantine is increased in successive dosages is less than 5 mg of memantine. The term adverse event refers to any undesirable side effect or toxic effect associated with memantine. In relation to embodiments of this type, it is preferable that the dose of memantine is increase by an increment of about 0.25 to about 0.5 mg each day until the maintenance dose is reached.

The present invention may be described in the following examples. These examples are given only to provide direction and guidance in how to make and use the invention, and are not intended to limit the scope of the invention in any way.

EXAMPLE 1

Unless otherwise indicated, all steps in this procedure are carried out at room temperature. Table 1, below, shows the amounts of each ingredient used in this procedure. In a 2 cubic foot PK V-Blender, memantine HCl (Conti BPC N.V., Landen, Belgium) and microcrystalline Cellulose (Avicel PH101, FMC Corporation, Philadelphia, Pa.) are combined and mixed for 105 revolutions. The mixture is then milled with a Quadro Comil using a 0.024-inch (0.6-mm) screen and a square impeller. The milling step is repeated for a second time. The milled mixture is then filled into polyethylene lined drum.

In a 10 cubic foot PK V-blender, the milled memantine HCl/microcrystalline cellulose mixture is combined with the Lactose, microcrystalline cellulose (Avicel PH302, FMC Corporation, Philadelphia, Pa.), Crosscarmellose sodium (FMC Biopolymer, Philadelphia, Pa.), and colloidal silicon dioxide (Cab-O-Sil, Cabot Corporation, Tuscola, Ill.). The mixture is mixed for 95 revolutions and then passed through the 0.039-inch (1-mm) screen using the Quadro Comil with round impeller. The mixture is placed back into the V-blender and mixed for 228 revolutions. The Magnesium Stearate is manually passed through a 30-mesh (0.6-mm) screen and added into the V-blender. The mixture is mixed for final 57 revolutions. For the validation batches, blend samples are taken at 10 different locations (See Figure using stainless steel side sample thief with 0.5-cc insert. The blend samples are tested for blend uniformity prior to the compression of tablets. The blend is charged into polyethylene lined drums.

The tablet press equipment is set up with appropriate punch tooling to produce each of the four dose strengths. The upper punches are embossed with the appropriate logo, and the lower punches are bisected (tablet scoring).

The Memantine HCl blend is manually scooped from the polyethylene lined drum into the press hopper. The press is then set to the appropriate compression parameters to produce the required in-process tablet specifications. The blend is compressed at the appropriate compression rate to produce the required tablets lot size per dose strength. During the compression, the tablet weight and hardness are monitored periodically as the tablets are collected in a polyethylene-lined drum. For the validation batches, tablet samples are collected at minimum frequency of beginning, middle and end of the compression run. These samples are tested for content uniformity prior to the film-coating step.

The coating procedure is carried out with the ingredients shown in the amounts listed in Table 2. The coating equipment is set up with a 36-inch pan and three spray guns. The first coating suspension is prepared with Colorcon's (West Point, Pa.) Opadry Purple 03B10434 at 12% (w/w). This material contains titanium dioxide, FD&C Blue #2 and Red #40 (purple colorant), hydroxypropyl methylcellulose (HPMC; polymer carrier) and polyethylene glycol (PEG) 400 (plasticizer). The second suspension is prepared with Opadry Clear YS-1-19025-A material at 5% (w/w). This clear coating material contains HPMC and PEG.

After the coating pan is charged with 50 kg of appropriate tablet dose strength, the coating equipment is set up with the appropriate parameters detailed in the coating batch records. The purple coating solution is applied onto the tablets at the appropriate spray rate until the required amount is achieved. The film-coat is applied at 4% of core weight for 5 mg dose and at 3% for the 10-20 mg dose tablets. Using the same coating parameters, a final coat with the clear coating solution at 0.5% of each core weight is applied. The tablets are allowed to dry in the coating pan for a short period prior to transfer into a polyethylene-lined drum.

TABLE 1

Ingredient Quantities for 175 Kg Lots of Memantine HCl Blend

| Part | Description | Ingredient | Concentration (% w/w) | Quantity for 175 kg Lot (kg) |
|---|---|---|---|---|
| Part I | Milling | Memantine HCl | 4.00 | 7.00 |
|  |  | Avicel PH101 | 4.00 | 7.00 |
| Part II | Blending | Part I | — | — |
|  |  | Lactose Fast Flo | 69.61 | 121.82 |
|  |  | Avicel PH302 | 16.84 | 29.47 |
|  |  | Croscarmellose Sodium | 5.00 | 8.75 |
|  |  | Cab-O-Sil | 0.25 | 0.44 |
|  |  | Magnesium Stearate | 0.30 | 0.52 |

TABLE 2

Ingredient Quantities for Film Coating of
50 Kg of Memantine HCl Tablets

| Film Coating Ingredient | Required Amounts (kg) for 50 Kg of Tablets for Coating | |
|---|---|---|
| | 5 mg dose | 10, 15, 20 mg doses |
| Purple Coating | | |
| Opadry Purple 03B10434 | 2.00 | 1.50 |
| Water | 14.67 | 11.00 |
| Glaze Coating | | |
| Opadry Clear YS-1-19025-A | 0.25 | 0.25 |
| Water | 4.75 | 4.75 |

EXAMPLE 2

Using the packaging hereinabove described a patient suffering from glaucoma, is administered a tablet comprising 5 mg of memantine, prepared according to example 1, daily for two weeks. No misdosing occurs. After two weeks, a tablet comprising 10 mg of memantine is administered daily for as long as the drug is needed.

EXAMPLE 3

Using the packaging hereinabove described a patient suffering from glaucoma, is administered a tablet comprising 5 mg of memantine, prepared according to example 1, daily for two weeks. No misdosing occurs. After two weeks, a tablet comprising 10 mg of memantine is administered daily for two weeks. At the beginning of the fourth week of the treatment, a tablet comprising 15 mg of memantine, prepared according to Example 1, is administered daily for two weeks. No misdosing occurs. At the beginning of the sixth week of treatment, a tablet comprising 20 mg of memantine is administered daily for as long as the drug is needed.

EXAMPLE 4

Using the packaging hereinabove described a patient suffering from glaucoma, is administered a tablet comprising 2 mg of memantine is administered for one week. The patient then receives a tablet comprising a 4 mg dose for one week. The dose is increased by 2 mg each week until a 10 mg dose is reached at the beginning of the fifth week. During the first four weeks of administration of the drug, improved tolerance of the drug is observed. The tablet comprising 10 mg of memantine is administered daily for as long as the drug is needed.

EXAMPLE 5

Using the packaging hereinabove described a patient suffering from glaucoma, is administered a tablet comprising 2 mg of memantine is administered for one week. The patient then receives a tablet comprising a 4 mg dose for one week. The dose is increased by 2 mg each week until a 20 mg dose is reached at the beginning of the tenth week. During the first nine weeks of administration of the drug, improved tolerance of the drug is observed. The tablet comprising 20 mg of memantine is administered daily for as long as the drug is needed.

EXAMPLE 6

Using the packaging hereinabove described a patient suffering from glaucoma, is administered a tablet comprising 5 mg of memantine, prepared according to example 1, daily for two weeks. No misdosing occurs. After two weeks, a tablet comprising 10 mg of memantine is administered daily for two weeks. At the beginning of the fourth week of the treatment, a tablet comprising 15 mg of memantine, prepared according to Example 1, is administered daily for as long as the drug is needed. No misdosing occurs.

Although there has been hereinabove described a specific Memantine titration/compliance dosage form in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclose herein. Accordingly, any and all modifications, variations or equivalent arrangements which may occur to those skilled in the art, should be considered to be within the scope of the present invention as defined in the appended claims.

What is claimed is:

1. A method for enabling compliance with a regimen of changing dosage of medication, the method comprises the steps of:
    providing a backing having an array of receivers, said array including a plurality of columns and a plurality of rows;
    disposing a plurality of sets of tablets in the receivers, each tablet in a set having a common dose of medication and a different dose than a tablet of a different set, each set being disposed in receivers of one of an adjacent row and an adjacent column;
    different sets of tablets are disposed in different rows, each row being indicated as a successive week, each column being indicated as a different day of the week, sets of tablets having increased doses being disposed in receivers of rows indicated as successive weeks; and
    providing indicia adjacent the columns and rows indicating common days and successive weeks.

2. A method of treating a human patient to reduce damage to retinal ganglion cells associated with glaucoma, said method comprising providing a titration package for enabling compliance with a regimen of changing dosage of medication over a period of time, the package comprising:
    a backing having an array of receivers, said array including a plurality of columns and a plurality of rows;
    a plurality of sets of tablets, each tablet in a set having a common dose of the medication and a different dose than a tablet of a different set, each set being disposed in receivers of one of an adjacent row and an adjacent column; different sets of tablets are disposed in different rows, each row being indicated as a successive week, each column being indicated as a different day of the week, sets of tablets having increased doses being disposed in receivers of rows indicated as successive weeks; and
    indicia disposed adjacent the columns and rows for displaying common days and successive weeks.

3. The method according to claim 2 wherein the medication comprises Memantine.

4. The method according to claim 2 wherein the sets of tablets have 5 mg, 10 mg, 15 mg, and 20 mg doses of Memantine.

5. The method according to claim 2 wherein different sets of tablets are disposed in different columns, each column being indicated as a successive week, each row being indicated as a different day of the week.

6. The method according to claim 5 wherein sets of tablets have increased doses are disposed in receivers of columns indicated as successive weeks.

* * * * *